United States Patent [19]
Street

[11] Patent Number: 6,115,627
[45] Date of Patent: Sep. 5, 2000

[54] INTRACARDIAC PREDICTOR OF IMMINENT ARRHYTHMIA

[75] Inventor: Anne M. Street, Sunnyvale, Calif.

[73] Assignee: Pacesetter, Inc., Sunnyvale, Calif.

[21] Appl. No.: 09/289,206

[22] Filed: Apr. 9, 1999

[51] Int. Cl.[7] .................................................. A61B 5/0468
[52] U.S. Cl. ............................................................. 600/515
[58] Field of Search ................................ 600/515, 509, 600/516, 517, 518; 607/5, 14

[56] References Cited

U.S. PATENT DOCUMENTS

| | | | |
|---|---|---|---|
| 4,754,753 | 7/1988 | King | 128/699 |
| 4,832,038 | 5/1989 | Arai et al. | 128/670 |
| 4,862,361 | 8/1989 | Gordon et al. | 364/413.06 |
| 5,042,497 | 8/1991 | Shapland | 128/696 |
| 5,109,862 | 5/1992 | Kelen et al. | 128/702 |
| 5,265,617 | 11/1993 | Verrier | 128/704 |
| 5,425,749 | 6/1995 | Adams | 607/5 |
| 5,447,519 | 9/1995 | Peterson | 128/705 |
| 5,571,142 | 11/1996 | Brown et al. | 607/5 |
| 5,749,900 | 5/1998 | Schroeppel et al. | 607/4 |
| 5,755,671 | 5/1998 | Albrecht et al. | 600/516 |

OTHER PUBLICATIONS

Lund, et al.; Recovery of beat–to–beat variations of QRS; Medical & Biological Engineering & Computing; Jul. 1998; pp. 438–444.

*Primary Examiner*—Scott M. Getzow
*Attorney, Agent, or Firm*—Steven M. Mitchell

[57] ABSTRACT

A medical device includes a sensing unit for creating digital data representing the electrical activity of a heart and a controller for, among other things, predicting the onset of an arrhythmia in the heart. From the digital data created by the sensing unit, the controller extracts data that represents the QRS complex of the heart cycle over several cardiac cycles and calculates the power spectrum for each QRS complex. Then, for each QRS complex, the controller calculates the fraction of energy in the power spectrum that falls within one or more frequency bands. The controller than calculates variance of these energy fractions over a number of cardiac cycles. A change, such as a decrease, in the variance presages the onset of an arrhythmia.

33 Claims, 3 Drawing Sheets

INTRACARDIAC PREDICTOR OF IMMINENT ARRHYTHMIA

BACKGROUND OF THE INVENTION

1. Field of the Invention

The present invention is directed to a method and apparatus for predicting the onset of a heart arrhythmia.

2. Background

Medical devices such as pacemakers and implantable cardioverter defibrillators (ICDs) monitor the electrical activity of a patient's heart and detect arrhythmias. Such devices monitor electrical activity in the atria, the ventricles, or both the atria and ventricles. Often such devices initiate some type of electrical therapy upon detection of an arrhythmia. For example, such devices may provide bradycardia pacing, antitachycardia pacing, cardioversion or defibrillation therapy.

A disadvantage of initiating treatment only upon detection of a rapid heart rate or tachyarrhythmia is that some treatments require a relatively lengthy preparation time. This is especially true of treatments for arrhythmias involving the ventricles of the heart, i.e. ventricular fibrillation or ventricular tachycardia, which are particularly dangerous and often fatal if not treated. For example, a typical treatment for ventricular fibrillation is to apply a high voltage shock to the heart. Generally, this involves precharging a capacitor, which can take as long as thirty seconds, thus delaying treatment for as long as thirty seconds following onset of the fibrillation. Medical devices that predict the onset of a heart arrhythmia would be advantageous by having therapy primed and ready for delivery at the onset of arrhythmia. It may also be possible to provide treatment to the heart that would prevent the onset of the arrhythmic event.

Many prior efforts to predict heart arrhythmias have focussed on long-term prediction of risk, that is, identifying people who are at risk of suffering heart arrhythmias and quantifying those risks. A common technique used in this long-term risk stratification is heart rate variability analysis derived from power spectral analysis of the heart's R—R intervals. The low frequency component of the power spectrum is attributed to the sympathetic input to the heart and the high frequency component is attributed to the respiratory cycle and vagal input. Decreased vagal tone is considered a marker for elevated arrhythmic risk. Recent efforts in short-term prediction of arrhythmias have centered on changes in electrogram features such as T wave alternans and patterns in the R—R intervals, or changes in the neural activity, similar to the techniques of long-term risk stratification. The instant invention looks instead at the morphology of the QRS complex recorded via an intracardiac electrode. The activation complex morphology is represented by the power spectrum of the complex and changes therein are analyzed to predict the onset of a heart arrhythmia.

The interest in QRS morphology changes is in part due to the work by K. Lund et al. showing cyclic variation in body surface electrogram morphology due to respiration. His work also alludes to direct neural input to the ventricular myocardium and cyclic variations at that level, which influence beat-to-beat morphology. It can be inferred that a decrease in neural input would influence the cyclic changes in morphology.

SUMMARY OF THE INVENTION

An exemplary medical device embodying teachings of the present invention includes a sensing unit for creating digital data representing the electrical activity of a heart and a controller for controlling operation of the device. Among other things, the controller attempts to predict the onset of an arrhythmia in the heart. To do so, the controller extracts data representing the QRS complex and calculates its power spectrum. This is repeated for every heartbeat. Then, for each QRS complex, the controller calculates the fraction of energy in the power spectrum that falls within one or more frequency bands. The controller finally calculates the variance in these energy fractions over several QRS complexes. A change, such as a decrease, in the variance presages the onset of an arrhythmia.

Upon determining that an arrhythmia is imminent, the exemplary medical device can take one or more of several possible actions. Such actions include preparing a treatment that will be administered upon actual occurrence of the arrhythmia. Other actions include immediately applying a treatment to the heart in an attempt to avoid occurrence of the arrhythmia, or warning the patient or medical personal of the imminent onset of the arrhythmia.

DETAILED DESCRIPTION OF A PREFERRED EMBODIMENT

The following description of a preferred embodiment of the invention is intended to be exemplary only. Although the embodiment of the invention described below is incorporated into an implantable cardiac device for monitoring, diagnosing, and/or treating a heart, the invention is not limited to use in such a device. Rather, the invention can be used with any type of cardiac device that monitors the electrical activity of the heart such as a bedside monitor or an automatic external defibrillator.

Figure 1:
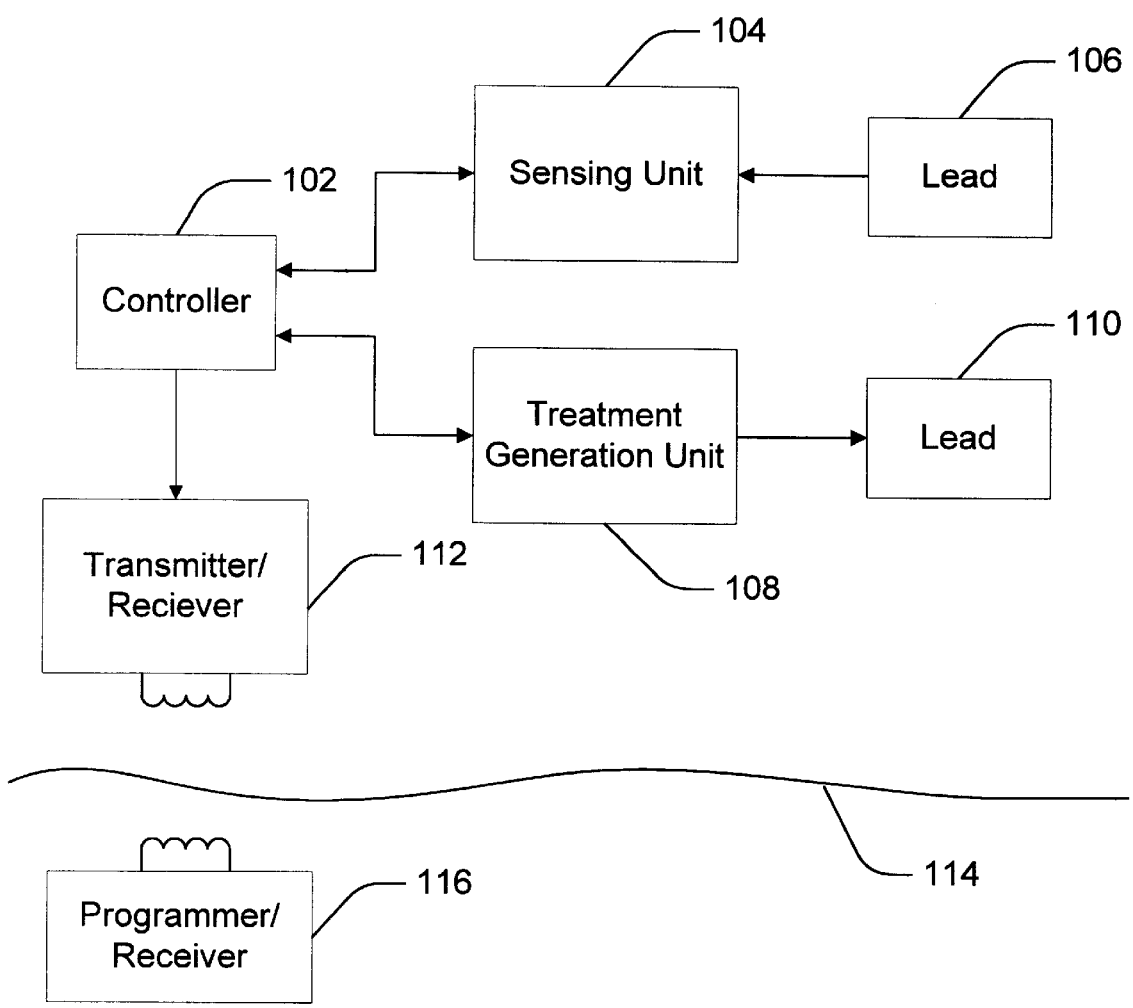
FIG. 1 is a block diagram of an exemplary embodiment of a cardiac device according to the present invention.

FIG. 1 illustrates an exemplary cardiac device 100 in which an exemplary embodiment of the invention is incorporated. The cardiac device 100 includes a controller 102 and a sensing unit 104 with heart lead 106. The cardiac device may also include a treatment generation unit 108 with heart lead 1 10 and a transmitter/receiver 1 12 for communicating with a programmer/receiver 116 that is external to the patient (not shown). (The patient's skin is illustrated as 114 in FIG. 1.) Although heart leads 106, 110 are illustrated as separate leads in FIG. 1, the sensing unit 104 and the treatment generation unit 108 may use the same heart lead or leads.

The controller 102, which is described in more detail below, controls overall operation of the device 100. The sensing unit 104 receives electrical signals representing the patient's heart activity via heart lead 106, filters those signals, and converts them into digital data. The sensing unit 104 then may store the digital data or otherwise make the data available to the controller 102. The controller 102 may communicate with the sensing unit 104 by, for example, providing parameters, data, and/or control or status signals to the sensing unit. Likewise, the sensing unit 104 may communicate with the controller 102 by providing parameters, data, and/or control or status signals to the controller.

The treatment generation unit 108 generates one or more electrical shocks that are delivered to the patient's heart (not shown) via a heart lead 110. The treatment generation unit 108 does so in accordance with data, parameters, and/or control or status signals it receives from the controller 102. The treatment generation unit 108 may also communicate with the controller 102 by, for example, providing parameters, data, and/or control or status signals to the controller.

Transmitter/receiver 112 is capable of receiving data from or transmitting data to the programmer/receiver 116, which is located external to the patient. Thus, data regarding the patient's heart activity, data regarding operation of the cardiac device 100, and other data can be transmitted through the patient's skin 114 to the programmer/receiver 116. In addition, new operational and data parameters, new program code, and other data can be transmitted from the programmer/receiver 116 through the patient's skin 114 to the transmitter/receiver 112.

Design and operation of a sensing unit 104, a treatment generation unit 108, a transmitter/receiver 112, and a programmer/receiver 116 are well known to people skilled in the art. Any suitable design can be used with the present invention. Because the details of such designs as well as their use and operation are well known, a detailed description of the sensing unit 104, treatment generation unit 108, transmitter/receiver 112, and programmer/receiver 116 will not be given here.

Figure 2:
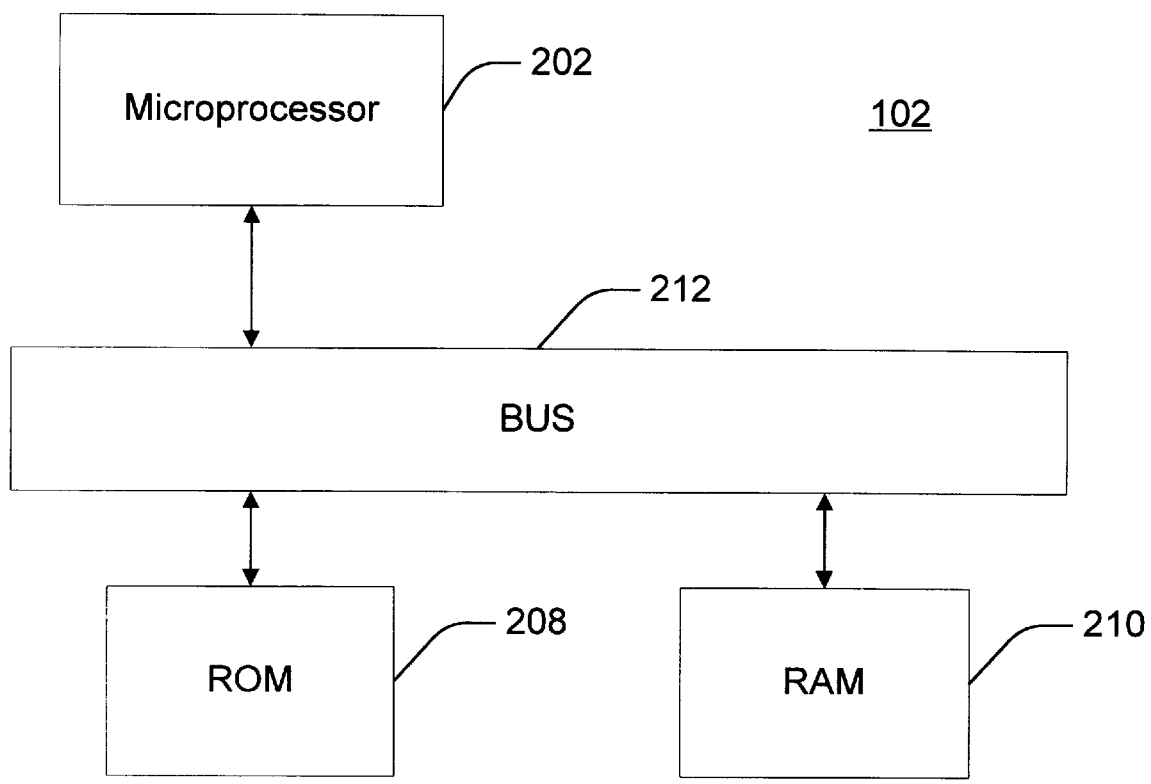
FIG. 2 is a block diagram of the controller of FIG. 1.

FIG. 2 illustrates an exemplary embodiment of the controller 102. As illustrated, the exemplary controller includes a microprocessor 202, a read only memory ("ROM") 208, a random access memory ("RAM") 210, and a bus 212. The ROM 208 contains program code, which is loaded into the RAM 210 by appropriate control circuitry (not shown) via the bus 212. The microprocessor 202 then executes the program code stored in the RAM 210.

The program code defines routines that the controller 102 performs. Such routines may perform functions such as controlling overall operation of the cardiac device 100; transmitting data to or receiving data from an external source via transmitter/receiver 112; controlling the sensing unit 104; analyzing digital data representing the electrical activity of the patient's heart (not shown) sensed by the sensing unit 104 to diagnose a cardiac arrhythmia; selecting an appropriate treatment for the patient's heart; and/or controlling the treatment generation unit 108 and causing it to apply a treatment to the patient's heart. Design and implementation of program code to perform such functions are well know to those skilled in the art and, accordingly, will not be further described. The program code also includes routines for predicting onset of a heart arrhythmia.

Figure 3:
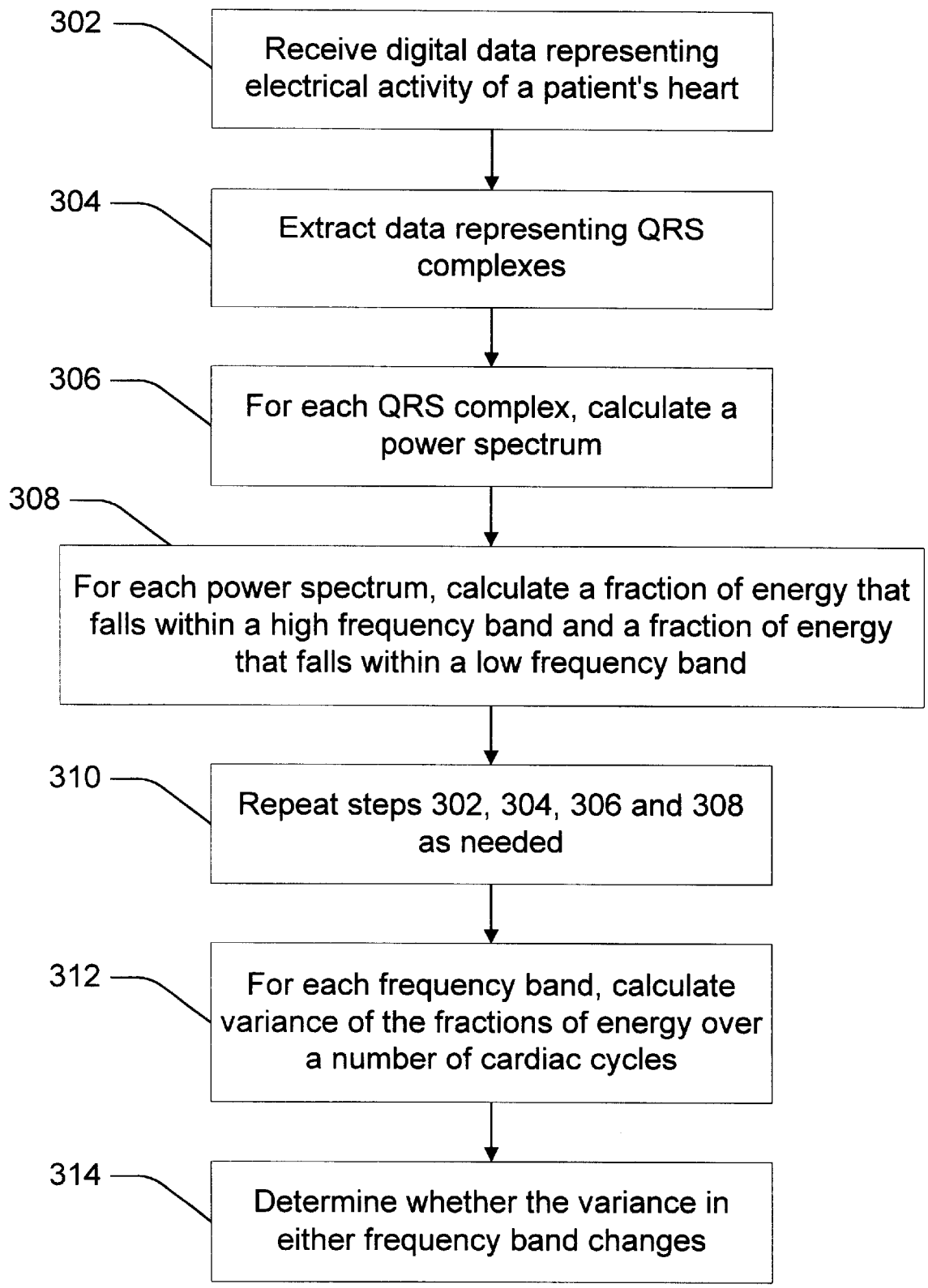
FIG. 3 is a flow chart illustrating operation of the microprocessor of FIG. 2.

FIG. 3 is a flowchart illustrating an exemplary embodiment of program code for predicting onset of an arrhythmia according to the teachings of the present invention. At step 302, the program code receives digital data representing the electrical activity of a patient's heart. As discussed above, the digital data is created by the sensing unit 104, which receives an analog signal representing the electrical activity of the patient's heart and digitizes that signal. At step 304, the program code extracts data representing a QRS complex of a cardiac cycle from the received digital data. If the digital data received at step 302 represents multiple cardiac cycles, the program code extracts data representing a QRS complex from each such cardiac cycle at step 304. At step 306, the program code calculates the power spectrum for each data set representing a QRS complex extracted at step 304. At step 308, the program code calculates the fraction of energy found in a low frequency band and the fraction of energy found in a high frequency band of each power spectrum calculated at step 306. The low frequency band is preferably 0 to 25 Hertz, and the high frequency band is preferably 25 to 62.5 Hertz. Other selections of frequency bands may also be used. Thus, by step 306, the program code has calculated the fraction of energy in a low frequency band and a high frequency band for one or more QRS complexes in the heart activity data created by the sensing unit 104. Steps 302, 304, 306, and 308 are repeated as necessary to calculate power spectrum and energy fractions for a number of QRS complexes (step 310).

Once the program code has calculated the fraction of energy in a low frequency band and a high frequency band for a number of QRS complexes, preferably approximately fifty, the program code calculates variance of the fractions of energy in the low frequency band and variance of the fractions of energy in the high frequency band over those complexes at step 312. The program code then determines whether variance in either frequency band has changed at step 314. A decrease in the variance in either frequency band indicates an impending heart arrhythmia.

In practice, the medical device 100 does not predict onset of an arrhythmia upon detecting only a slight decrease in the variance but does so only if the decrease in the variance exceeds a predetermined threshold. Preferably, that threshold is determined on a patient-by-patient basis. Alternatively, thresholds can be determined for particular patient categories depending on, for example, the patient's age, sex, medical history, body weight, or other such factors. One method of determining the threshold for a single patient is to monitor the heart activity of the patient in a clinical setting and use collected data regarding the patient's heart activity to determine a threshold that indicates likely onset of an arrhythmia. Likewise, a method of determining the threshold for a category of patients is to monitor the heart activity of a group of patients who fall within the category and use collected data regarding the heart activity of those patients to determine a threshold that indicates likely onset of an arrhythmia for a person who falls within that category. Once a threshold is determined for a patient, that threshold is programmed into the medical device 100, for example, using the programmer/receiver 116, prior to using the medical device 100 with the patient.

Many methods and devices are known to those skilled in the art for identifying and extracting data representing a QRS complex, calculating the power spectrum of digital data representing a QRS complex, calculating the fraction of energy that falls within a particular frequency band of a power spectrum, and calculating variance. Accordingly, such methods and devices are not described in detail here, and any such method or device can be used with the present invention. One commercially available product for calculating power spectrum, calculating the fraction of energy that falls within a frequency band of the power spectrum, and calculating variance is Matlab® by Math Works.

If an impending cardiac arrhythmia is predicted, the medical device 100 can take one or more of several possible actions. One such action is to start preparations immediately for a treatment to be delivered to the heart upon actual onset of the arrhythmia. For example, if the expected arrhythmia involves the ventricles of the heart, charging of a capacitor for delivering a cardioverting or defibrillating shock to the heart can be started immediately. In such a case, the controller 102 would cause the treatment generation unit 108 to begin charging a capacitor (not shown). Thereafter, upon actual detection of the arrhythmia, controller 102 would cause the treatment generation unit 108 to deliver a cardioverting or defibrillating shock to the heart via lead 110.

Another action that can be taken in anticipation of a predicted arrhythmia is to initiate a treatment designed to prevent onset of the arrhythmia. The controller 102 would cause the treatment generation unit 108 to deliver a treatment to the heart via lead 110 prior to actual onset of the arrhythmia. Yet another action that can be taken is to effect some type of warning that an arrhythmia is expected. For example, the controller 102 could cause the transmitter/receiver 112 to transmit a signal to the programmer/receiver 116 indicating imminent onset of an arrhythmia. A warning indicator such as an audible sound or electrical stimulation of a muscle of the patient could then be delivered.

The above description of preferred embodiments of the invention is not intended to be limiting. Persons skilled in the art will appreciate that modifications may be made to the preferred embodiments and alternative embodiments may be created that are within the scope and spirit of the invention. For example, although the preferred embodiment of the invention is described above as being incorporated into a medical device that is implantable within a patient, the invention can be incorporated into devices that are external to the patient. Also, a device into which the invention is incorporated need not include a transmitter/receiver 112, a programmer/receiver 116, or a treatment generation unit 108. In addition, although the preferred embodiment of the invention described above calculates fractions of energy found in two frequency bands, an alternative embodiment of the invention could calculate fractions of energy found in only one frequency band. Alternatively, an embodiment of the invention could calculate fractions of energy found in more than two frequency bands. In the preferred embodiment described above, onset of an arrhythmia is predicted if the variance of energy fractions in the power spectrums of multiple QRS complexes decreases over time. Alternatively, other changes in the variance could be used to predict the onset of an arrhythmia, such as an increase in the variance. Although the preferred embodiment of the invention is a software-based system in which a microprocessor operates under control of software, the invention could be implemented using logic circuits or a combination of software and logic circuits.

These and other variations of the preferred embodiment described above are within the scope and spirit of the invention, and the claims are intended to embrace all such variations. Thus, the invention is limited only by the following claims.

What is claimed is:

1. A method for predicting onset of a heart arrhythmia comprising:
    (a) receiving digital data representing electrical activity of a patient's heart during a cardiac cycle;
    (b) calculating a power spectrum of a portion of said digital data;
    (c) calculating a fraction of energy in said power spectrum that falls within a particular frequency band of said power spectrum;
    (d) repeating said steps (a),(b), and (c) over a plurality of cardiac cycles;
    (e) calculating variance of said fractions of energy calculated in said step (c) over said plurality of cardiac cycles; and
    (f) determining whether said variance changes over said plurality of cardiac cycles.

2. The method of claim 1, wherein said particular frequency band is a low frequency band.

3. The method of claim 2 wherein said low frequency band is 0 Hertz to 25 Hertz.

4. The method of claim 1 wherein said particular frequency band is a high frequency band.

5. The method of claim 4 wherein said high frequency band is 25 Hertz to 62.5 Hertz.

6. The method of claim 1 wherein said step (f) determines whether said variance decreases over said plurality of cardiac cycles.

7. The method of claim 1 wherein said step (d) repeats said steps (a),(b), and (c) over at least fifty cardiac cycles.

8. The method of claim 1 further comprising the step of effecting a warning indicating onset of a heart arrhythmia if a change in said variance is detected at said step (f).

9. The method of claim 1 further comprising the step of preparing a treatment if a change in said variance is detected at said step (f).

10. The method of claim 9 wherein said step of preparing a treatment includes precharging a high voltage capacitor for delivering an electric shock to said heart.

11. The method of claim 1 further comprising the step of applying a treatment to said heart if a change in said variance is detected at said step (f).

12. The method of claim 11 wherein said step of applying a treatment includes applying antiarrhythmia pacing.

13. The method of claim 11 wherein said step of applying a treatment includes applying neural stimulation.

14. The method of claim 1 wherein
    said step (c) further comprises calculating a fraction of energy in said power spectrum that falls within each of a plurality of frequency bands of said power spectrum;
    said step (e) further comprises calculating, for each said frequency band, variance of said fractions of energy calculated in said step (c); and
    said step (f) further comprises determining whether any of said variances calculated in said step (e) changes over said plurality of cardiac cycles.

15. The method of claim 14 wherein said plurality of frequency bands includes a low frequency band and a high frequency band.

16. The method of claim 15 wherein said low frequency band is 0 Hertz to 25 Hertz and said high frequency band is 25 Hertz to 62.5 Hertz.

17. The method of claim 1 wherein said ventricle activity is a QRS complex.

18. The method of claim 1 wherein said step (b) includes calculating a power spectrum of a portion of said digital data that represents ventricle activity of said heart during said cardiac cycle.

19. A medical device comprising:
    means for creating digital data representing electrical activity of a patient's heart;
    means for calculating power spectrums of portions of said digital data;
    means for calculating fractions of energy of said power spectrums that fall within a particular frequency band for each of said plurality of cardiac cycles;
    means for calculating variance of said fractions of energy calculated over said plurality of cardiac cycles; and
    means for determining whether said variance changes over said plurality of cardiac cycles.

20. The device claim 19, wherein said particular frequency band is a low frequency band.

21. The device of claim 20 wherein said low frequency band is 0 Hertz to 25 Hertz.

22. The device of claim 19 wherein said particular frequency band is a high frequency band.

23. The device of claim 22 wherein said high frequency band is 25 Hertz to 62.5 Hertz.

24. The device of claim 19 wherein said means for determining whether said variance changes over said plurality of cardiac cycles determines whether said change is a decrease in variance.

25. The device of claim 19 further comprising means for effecting a warning indicating onset of a heart arrhythmia if a change in said variance is detected by said means for determining whether said variance changes over said plurality of cardiac cycles.

26. The device of claim 19 further comprising means for preparing a treatment if a change in said variance is detected by said means for determining whether said variance changes over said plurality of cardiac cycles.

27. The device of claim 26 wherein said means for preparing a treatment precharges a capacitor for delivering an electric shock to said heart.

28. The device of claim 19 further comprising means for applying a treatment to said heart if a change in said variance is detected by said means for determining whether said variance changes over said plurality of cardiac cycles.

29. The device of claim 19 wherein:

said means for calculating fractions of energy further calculates fractions of energy in said power spectrum that fall within each of a plurality of frequency bands of said power spectrum;

said means for calculating variance further calculates, for each said frequency band, variance of said fractions of energy calculated by said means for calculating fractions of energy; and said means for determining whether said variance changes further determines whether any of said variances calculated by said means for calculating variance changes over said plurality of cardiac cycles.

30. The device of claim 29 wherein said plurality of frequency bands includes a low frequency band and a high frequency band.

31. The device of claim 30 wherein said low frequency band is 0 Hertz to 25 Hertz and said high frequency band is 25 Hertz to 62.5 Hertz.

32. The device of claim 19 wherein said ventricle activity is a QRS complex.

33. A machine-readable media containing program code for causing a processor to perform a process comprising:

receiving digital data representing electrical activity of a heart for a plurality of cardiac cycles;

for each of said plurality of cardiac cycles, extracting data from said received digital data that represents ventricle activity of said heart;

for each of said plurality of cardiac cycles, calculating a power spectrum of said extracted data representing said ventricle activity of said heart;

for each of said plurality of cardiac cycles, calculating a fraction of energy in said power spectrum that falls within a particular frequency band;

calculating variance of said fractions of energy over said plurality of cardiac cycles; and determining whether said variance changes over said plurality of cardiac cycles.

* * * * *